(12) United States Patent
Ibbotson et al.

(10) Patent No.: US 9,581,593 B2
(45) Date of Patent: Feb. 28, 2017

(54) MICRO-SENSOR BASED TEST APPARATUS

(71) Applicant: Microvisk Limited, St Asaph (GB)

(72) Inventors: Robert Ibbotson, St Asaph (GB); Vladislav Djakov, St Asaph (GB); Richard Dunn, St Asaph (GB)

(73) Assignee: Microvisk Limited, St. Asaph (GB)

( * ) Notice: Subject to any disclaimer, the term of this patent is extended or adjusted under 35 U.S.C. 154(b) by 90 days.

(21) Appl. No.: 14/379,170

(22) PCT Filed: Feb. 15, 2013

(86) PCT No.: PCT/GB2013/050360
§ 371 (c)(1),
(2) Date: Aug. 15, 2014

(87) PCT Pub. No.: WO2013/121211
PCT Pub. Date: Aug. 22, 2013

(65) Prior Publication Data
US 2015/0017067 A1 Jan. 15, 2015

(30) Foreign Application Priority Data

Feb. 16, 2012 (GB) .................................. 1202694.4

(51) Int. Cl.
*G01N 33/52* (2006.01)
*G01N 33/543* (2006.01)
*G01N 33/86* (2006.01)

(52) U.S. Cl.
CPC ....... *G01N 33/54373* (2013.01); *G01N 33/86* (2013.01)

(58) Field of Classification Search
CPC .................... G01N 2291/0427; G01N 29/022
See application file for complete search history.

(56) References Cited

U.S. PATENT DOCUMENTS

| 2004/0163953 A1* | 8/2004 | Bhullar | ............... C12Q 1/001 204/403.01 |
|---|---|---|---|
| 2005/0019212 A1 | 1/2005 | Bhullar | |
| 2007/0089987 A1 | 4/2007 | Neel | |

(Continued)

FOREIGN PATENT DOCUMENTS

| EP | 1195441 | 4/2002 |
|---|---|---|
| EP | 1318397 | 6/2003 |

(Continued)

OTHER PUBLICATIONS

International Search Report & Written Opinion, PCT/GB2013/050360. Apr. 17, 2003.

(Continued)

*Primary Examiner* — Dennis M White
(74) *Attorney, Agent, or Firm* — John V. Daniluck; Brian W. Chellgren; Bingham Greenebaum Doll LLP (57) ABSTRACT

There is provided a fluid test strip, comprising a micro-sensor formed on a substrate surface and a reagent deposition site formed on the substrate surface, operate to control the size and location of a reagent deposition. There is also provided a method of forming fluid test strip, comprising forming a micro-sensor on a substrate surface and forming a reagent deposition site on the substrate surface, operable to control the size and location of a reagent deposition.

19 Claims, 7 Drawing Sheets

(56) References Cited

U.S. PATENT DOCUMENTS

| | | | |
|---|---|---|---|
| 2007/0193882 A1 | 8/2007 | Dai et al. | |
| 2008/0261326 A1 | 10/2008 | Dudenhoefer | |
| 2011/0233059 A1 | 9/2011 | Guendig et al. | |
| 2011/0277193 A1* | 11/2011 | Smetana | B82Y 10/00 |
| | | | 850/56 |

FOREIGN PATENT DOCUMENTS

| | | |
|---|---|---|
| WO | 2008130920 | 10/2008 |
| WO | 2011133663 | 10/2011 |

OTHER PUBLICATIONS

Combined Search and Examination Report, GB1202694.4. Jun. 6, 2012.

* cited by examiner

MICRO-SENSOR BASED TEST APPARATUS

FIELD OF THE INVENTION

This invention relates to the integration of surface patterning for containment of reagent chemistry on a micro-sensor based test strip.

BACKGROUND OF THE INVENTION

Many chemical and biological reactions are used to provide diagnostics or other test functions in the areas of healthcare, industrial test and the like. These diagnostic tests typically involve introducing one or more reagents to a fluid under test (or one another) in a controlled manner, in order to provide accurate detection of one or more parameters of the reaction that takes place. Examples of such diagnostic tests include immunoassays, blood coagulation assays, and the like.

A particular example of a chemical or biological diagnostic test is a micro-sensor based test strip, where a test strip including the micro-sensors may be dipped into a fluid to be tested, or may include a test reaction chamber surrounding the micro-sensors to contain the reagents and fluid to be tested, where the test reaction chamber is filled with the fluid under test and one or more reagents. The test strip reagents may be deposited onto a test strip surface during manufacture, prior to use, which are then activated upon contact with the fluid under test or activate the fluid under test.

In such test strip sensors, it is particularly useful to control the placement of the reagent in relation to the test micro-sensor, such as on the micro-sensor or in close proximity, and in relation to the flow of the biological or chemical sample. Often this placement must be done with high precision (e.g. variance<25 microns).

Where a reagent is deposited during manufacture of the test strip, ready for activation upon contact with the fluid under test or the like, it is advantageous to reduce the number of process steps required to form a test strip, since these test strips can be manufactured in the millions. Moreover, to ensure the consistency of the results, the manufacture of the test strips should be consistent also. This is particularly the case for micro-sensor based test strips, as the tolerances for the reagent deposition can be very tight.

SUMMARY OF THE INVENTION

Embodiments of the present invention provide a fluid test strip, comprising a micro-sensor formed on a substrate surface and a reagent deposition site formed on the substrate surface, operable to control the size and location of a reagent deposition. A fluid test strip is a term used herein to inclusively describe a monolithically integrated test sensor module comprising the micro-sensor and a place to position a portion of reagent. They may include a test chamber or similar, to allow the micro-sensor based fluid test strip to contain and carry out a test in the vicinity of the reagent and/or micro-sensor. They may be reusable or once-use only, and may be used with a corresponding electronic reading device into which the fluid test strips may be inserted for taking a reading using a test strip.

More than one deposition site may be provided in the vicinity of one (or more) sensors, for example where multiple sensors are operating each with a different reagent, or where a single sensor is operating with multiple reagents. Each deposition site may or may not be in separate chambers or channels, according to reaction needs.

Optionally, the deposition site comprises a central island portion, annularly surrounded by a portion of non-existent surface material. Put another way, the deposition site may comprise a central island portion, annularly surrounded by at least one moat.

Optionally, the reagent deposition site(s) may be formed adjacent the micro-sensor, and/or in a predetermined shape beneficial to the operation of the micro-sensor.

Optionally, the predetermined shape of the one or more deposition site(s) may comprise a shape operable to encompass at least a portion of the micro sensor, or a respective micro sensor.

Optionally, the micro sensor may comprise a micro-cantilever, and the predetermined shape comprises a portion encompassing a sensitive portion of the micro sensor, such as a free end of a micro-cantilever based micro sensor.

Optionally, a portion of non-existent surface material may comprise a moat. Optionally, the fluid test strip may further comprise at least one fence, wherein a fence comprises a portion of the surface material annularly surrounding a portion of non-existent surface material.

Optionally, the at least one fence may comprise multiple moats and fences, each numbered in the range of 1 to 3.

Optionally, the at least one moat may comprise between one and three moats and the at least one fence may comprise between one and three fences.

Optionally, the micro-sensor is at least one micro-cantilever based sensor operable to detect changes in a fluid under test as a result of a reaction between the fluid under test and one or more reagents deposited in the deposition site Optionally, the reagent deposition site may comprise a fixed area, such as between 100 and 600 microns across. Any moats and/or fences may comprise up to 40% of the total deposition site area.

The deposition site may be formed dependent upon one or more of: a contact angle of the surface material; a volume of deposited reagent fluid; a hydrophilicity of the surface material; a hydrophobicity of the surface material; a surface energy of the surface material; a surface treatment of the surface material.

The at least one moat may comprise a portion of non-existent surface material. The number of fences and moats may be unequal. A final outer annular formation may comprise a moat. The central island portion may comprise a predetermined area of surface material substantially similar in thickness to the remaining substrate. A moat may comprise an (annular) area of removed surface material, where 'annular' herein may mean 'surrounding'—the actual shape may be random rather than circular, or any other regular encompassing shape, such as ellipsoid, and the like). A fence may comprise an annular area of non-removed surface material.

Optionally, the deposition site may be formed through etching, flow moulding or stamping the substrate to form the central island portion and at least one moat or portion of non-existent surface material. The deposition site may also be formed by a combination of the above manufacturing methods. The deposition site may equally be referred to as a pattern or patterning.

There is also provided a method of forming fluid test strip, comprising forming a micro-sensor on a substrate surface and forming a reagent deposition site on the substrate surface, operable to control the size and location of a reagent deposition.

There is also provided a test strip manufacturing apparatus arranged to carry out any of the described methods, and a computer-readable medium comprising instructions, which, when executed by a processor, cause the processor to carry out any of the described methods.

The method may further comprise applying a surface treatment to the substrate surface prior to or after formation of the deposition site, the surface treatment operable to enforce the operation of the deposition site.

These and other aspects of the invention will be apparent from and elucidated with reference to the embodiments described hereinafter.

Embodiments of the invention provide improved methods of placing reagents on a substrate, such as polymer.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

Because the illustrated embodiments of the present invention may for the most part be implemented using components and methods known to those skilled in the art, details will not be explained in any greater extent than that considered necessary for the understanding and appreciation of the underlying concepts of the present invention and in order not to obfuscate or distract from the teachings of the present invention.

Embodiments of the invention provide surface patterning formations for containment of reagent chemistry on a micro-sensor based test strip, particularly for example when the test strip and micro-sensor are monolithically integrated. The containment provided gives improvement in accuracy and precision of clinical tests carried out using a fluid test strip according to embodiments of the invention by providing highly repeatable position, shape, and surface area of the respective reagents during deposition, for a range of hydrophilic or hydrophobic surfaces, relative humidity and temperature (i.e. dynamic contact angle, because temperature drives the evaporation of the droplet at the edge as it starts to expand across the surface, so the higher the temperature, the faster the evaporation and the result is a smaller area of (dried) drop. This is in effect like a variation in contact angle on the surface material that produces variation in area of the dried reagent in the environment in which the test strip arrangements are produced).

Embodiments of the invention may therefore mitigate against the presence, or effects, of such things as surface defects, variation in manufacturing reagent drop dispense directional accuracy, and the like. The containment provided may also give improvement to the speed and yield of the test strip manufacturing process, by allowing accurate higher volume deposition of the reagents, thus negating the need for multiple lower volume/layer deposition of the reagents. Additionally the patterning formations can be used in conjunction with a hot plate to heat the substrate material to thereby increase the drying speed of the deposited reagent, therefore allowing higher volumes to be dispensed in a given time frame.

The patterning may also be used to guide reagent(s) into areas that could not be located otherwise. For example, in the case of using a test strip having one or more cantilever shaped sensors to measure the progress and/or eventual outcome of the reaction, channels around a cantilever sensor or along the cantilever may be reached without covering and/or sticking the cantilever down.

The patterning may also advantageously provide a basis for controlling the position of the reagent solids within the deposition. This is because, in a droplet expanding across a surface, the majority of solids are driven to the edge (giving a so called "coffee ring" deposition formation). However, by providing a containment of the droplet, this also provides a control of the extent to which the solids are driven. Moreover, embodiments of the invention may provide a further advantage in such situations, because controlling the extent of the deposition may prevent parts of the solids being left behind by a receding fluid deposition. Where the deposition is biological, the solids left outside the containment may have poor lifetime stability compared to solids kept within the containment that, for example, contains sugars to preserve the lifetime stability. Also, if the deposited solids comprise solids that can be denatured (e.g. proteins) when not fully encapsulated by the containment (i.e. "protective shell"), keeping them within the containment can ensure their integrity pre and post drying of the fluid deposition.

Control of the deposition of the one or more reagents involved may be required, in order to control a number of parameters that may materially affect the reaction used in the test strip. These parameters may include: the type of surface material or treatment being used, location of the surface treatment, surface area and uniformity. These parameters are often bound together and changes in one tend to produce changes in the others. By creating a patterned deposition site, it is possible to improve consistency of the tests by reducing this interdependence and gaining greater control over the different parameters individually.

To understand the need for an improved chemistry deposition site, it is important to understand the behaviour of fluid deposited onto a surface. Surfaces made from different materials generally have different surface energies and therefore reagents dispensed on the surfaces exhibit different contact angles and different lateral drop sizes for the same quantity of dispensed reagent fluid. It is also possible to have a range of different surface energies on the same material, for example by using different surface treatments or varying surface treatment parameters.

The form a small drop of fluid deposited on a surface material takes is dependent on the surface energy of the surface material onto which the fluid is being deposited, the properties of the fluid and the environment. Surface energy may be estimated using contact angle measurement, where hydrophilic or hydrophobic surfaces give contact angles of less than or more than 90 degrees respectively.

Figure 1:
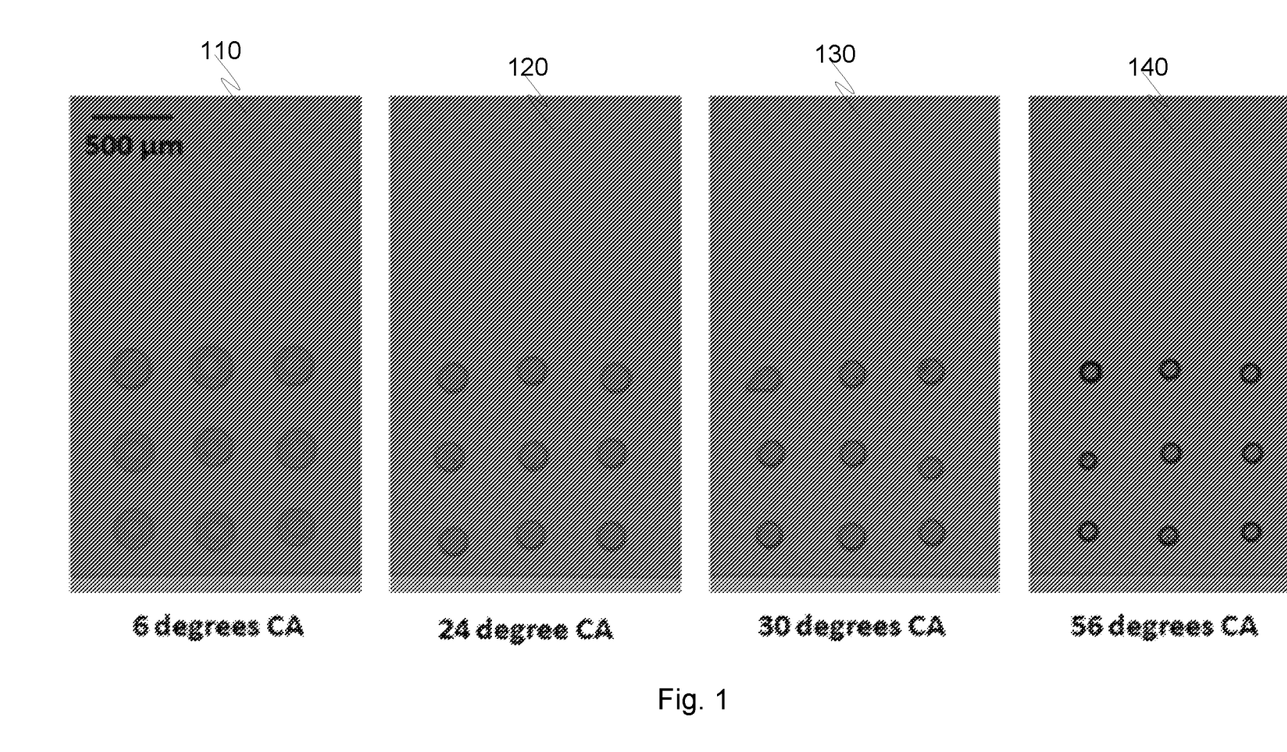
FIG. 1 comprises microscope images showing examples of the variation in deposition area for small, identical volumes of (e.g. reagent) deposition on polymer surface materials having different surface treatments which result in different contact angles.

To illustrate this point, depositions of chemicals were made onto four surfaces with different contact angles. Microscope images of the resultant depositions are shown in FIG. 1, in which images are seen of 3×3 spot arrays of identical spot volumes of chemistry deposited on four polymer surfaces which have undergone different surface treatments. In particular, there is shown: an example with a contact angle of 6° 110; an example with a contact angle of 24° 120; an example with a contact angle of 30° 130; and an example with a contact angle of 56° 140. It can be seen that, for any given reagent chemistry, as the contact angle on the surface material reduces, the diameter of the resultant droplet increases, i.e. it spreads into a larger area and flatter drop.

Figure 2:
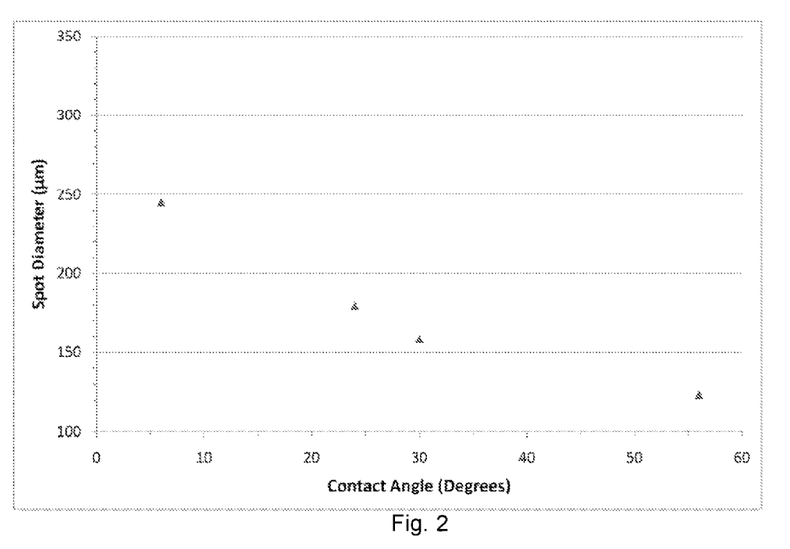
FIG. 2 plots the variation in deposition areas of FIG. 1 against contact angles.

The significant variation in droplet deposition shape and size in FIG. 1 shows there is a need for a method of forming deposition sites which can help control the variation in the area of deposited chemistry on surfaces with different contact angles, and it has been found that creating suitably formed deposition site(s) provides a solution to this problem. The particular formation of the deposition sites may vary according to various external parameters, as described in more detail below. FIG. 2 shows data extracted from FIG. 1 plotted on a graph for deposition diameter vs. contact angle on a polymer surface.

An example of the present invention particularly relates to a micro-sensor based blood coagulation assay to measure the Prothrombin Time (PT) of a blood sample (i.e. blood is the fluid under test). This example may consist of a micromechanical test sensor (comprising one or more sensor elements) formed on a substrate (e.g. die) located or to be located in a capillary channel. A reagent may be deposited and dried directly adjacent the one or more sensor elements, such that the flow of blood down the capillary allows dissolution of the reagent in close proximity to the micro sensor carrying out the test on the blood sample. In this example the reagent needs to be controlled in terms of volume, area, and position in relation to the capillary and micro sensor to give high precision of the test. The position and area of the deposited reagent may be dependent on a number of factors, including: the deposition liquid (i.e. reagent) handling apparatus capabilities (e.g. accuracy of drop volume dispensation, drop dispense directional accuracy, and the like); the hydrophilicity/hydrophobicity of the surface material onto which the reagent is deposited (which may be measured as the Water Contact Angle (WCA)); and the dynamic contact angle (which is the degree of evaporation of the droplet due to environmental temperature and humidity, and the like). These elements can be quite variable, for example, the nozzle of the liquid handling apparatus may have random flight paths from the nozzle (within a given specification of the equipment) or additional inaccuracy may occur due to ageing and contamination of the nozzle tip. Also, the hydrophilicity or surface energy of a substrate on to which the micro-sensor is formed may vary/cause variation, due to surface modification, and can take a range of values (e.g. WCA between 5 and 60) dependent on the chemical bonds, thickness, and stability of the surface material or subsequent surface material processing (e.g. applying a very thin covering layer with different surface characteristics, or the like).

In the following examples of the micro-sensor test strip according to embodiments of the invention, the micro sensor is a micromechanical, cantilever based sensor, where the cantilever has a free end that operates within the fluid under test (e.g. blood), and reagents are deposited adjacent to the free end, to be mixed into the fluid under test close to the test sensor. An example of such a test sensor is a bimorph cantilever micro-sensor as disclosed in WO2005/054817. However, the invention is not limited to a particular form of micro-sensor. Instead, it applies to all forms of micro-sensors monolithically integrated with a place of deposition for one or more reagents.

Figure 3:
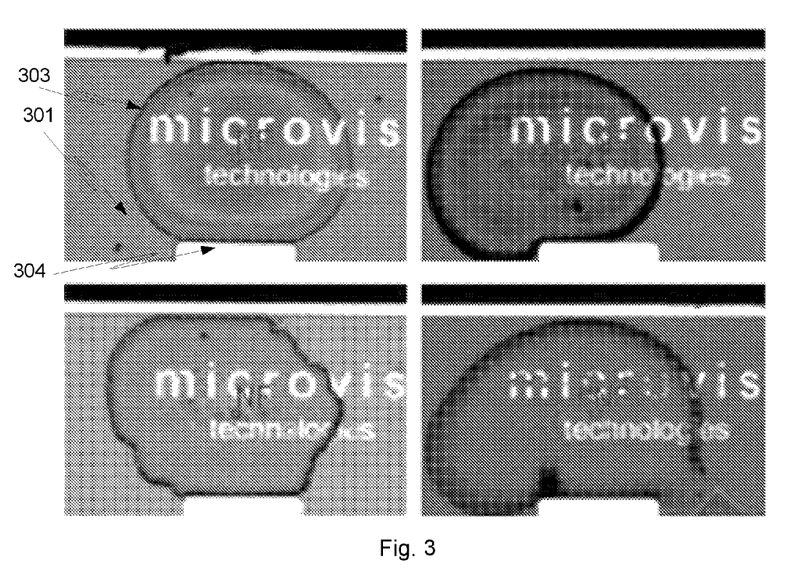
FIG. 3 comprises microscope images showing examples of the variation in deposition position and area for identical volumes of deposition on an unaltered polymer surface material adjacent to a micro-sensor of a test strip.

FIG. 3 shows four examples of such a micro-cantilever based test strip where a reagent 303 has been deposited on a surface material 301 adjacent the micro-sensor (not shown), where there is a slight gap 304 between the micro-sensor and the surface material 301. The four depositions show both large and subtle differences in location and surface area, where NF denotes the point of alignment of the deposition (i.e. where the deposition droplet was "aimed"). This figure comprises microscope images showing changes in both the location and surface area of depositions of identical volumes of reagent chemistry which cause variation in test results, and even these highly variable reagent depositions were only achieved by multiple layer depositions which resulted in a very slow manufacturing process.

Figure 4:
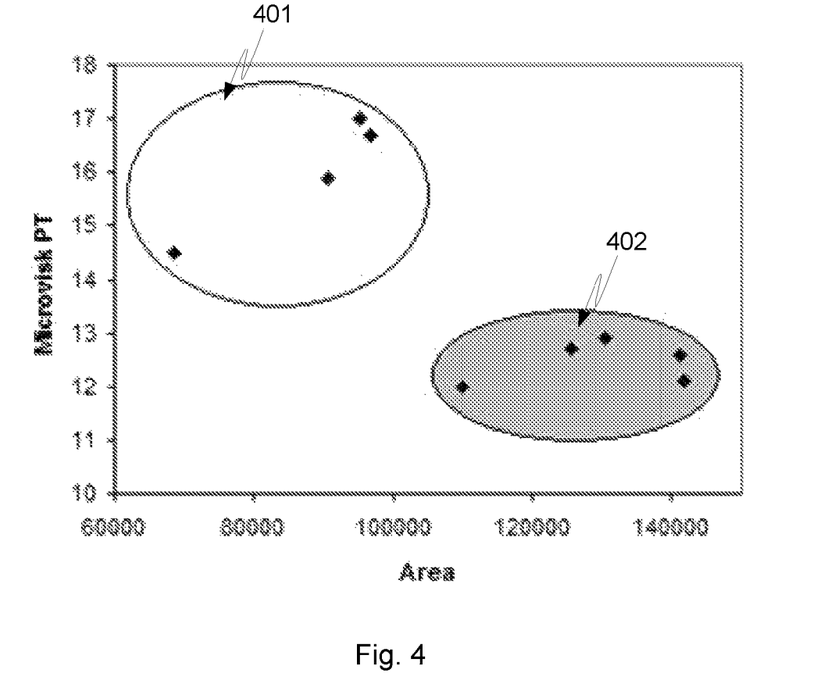
FIG. 4 shows the variation in measured Prothrombin Time (PT) against area of reagent deposition.

FIG. 4 shows the highly variable measured Prothrombin Time (PT) for repeat testing of INR (International Normalized Ratio) 2.2 blood samples against area of reagent deposition using the micro-sensor test strips without any surface material formation.

Figure 5:
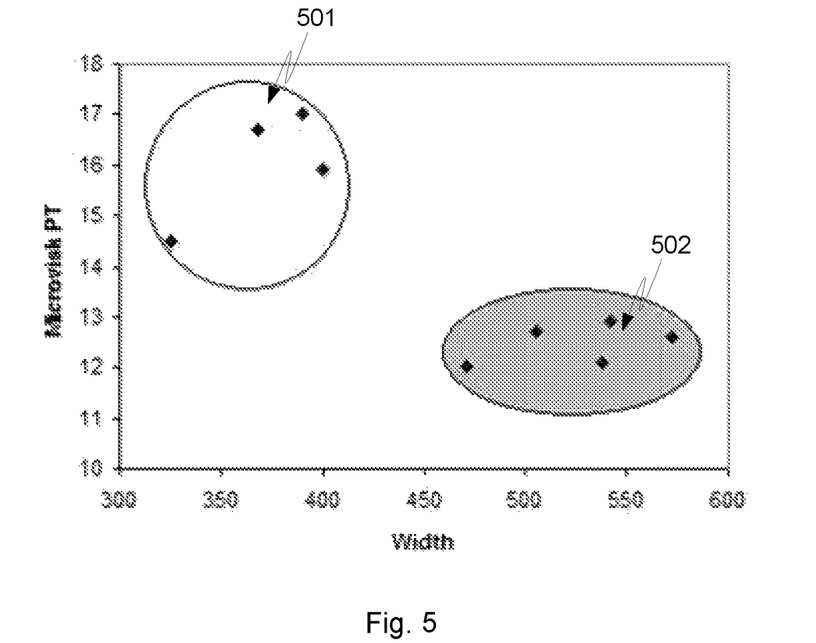
FIG. 5 shows the same PT times as FIG. 4, but compared by deposition width rather than area.

FIG. 5 shows the same results, but compared using deposition width instead of deposition area.

Both figures show the large variation in PT time, dependent on the variation of the deposition site area and width respectively, i.e. these graphs show the importance of controlling the deposition site size, and hence the importance of embodiments of the present invention. For example, if all PT results are used to calculate the percentage coefficient of variation (% CV) of the test, the resulting value is 14.4%. Visually, this can be seen to be due to the average PT time being in the centre of the two noted populations (401/402; 501/502) and therefore not representative of the data. Whereas, if results are selected by reagent area and width, for example, where reagent deposition site area >100000 pixels, then the % CV is equal to 3.1% showing that variation in reagent geometry in the channel creates imprecision in the assay.

For the particular use case of coagulation tests, in order to create a successful coagulation test, it is advantageous to provide controlled, low contact angles on surface material onto which reagent should be deposited. This improves the initial placement and flow of deposited reagent chemistry solution and other fluids across the surface material on the test strip. As can be clearly seen in FIG. 2, at low contact angles, small variations in the contact angle can result in larger variations in deposition diameter and therefore reagent surface area. For the case of reagent chemistry on a micro-sensor based test strip, it is advantageous to control the surface area over which the reagent chemistry is deposited, because that may in turn control how the reagent releases into the fluid under test in the overall test strip reagent chamber. If there is no independent control over the placement and volume of the reagent, and hence the volume deposited and the surface area of the resultant deposition, the test strips will be less consistent and precise. Furthermore, the surface area of the reagent deposition may be affected by the volume of reagent deposited.

Figure 6:
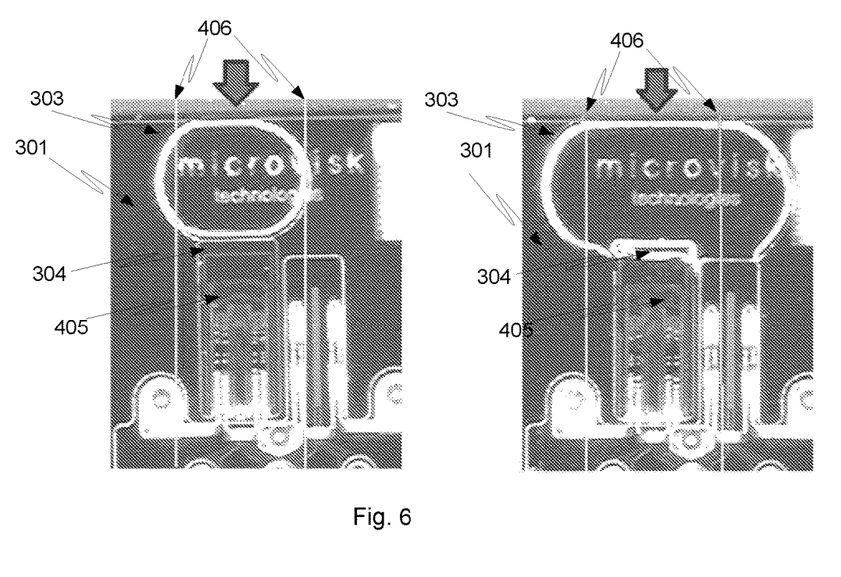
FIG. 6 shows the position and area of two examples of dried reagent for a blood coagulation assay deposited on an unaltered polymer surface material adjacent to a micro cantilever based micro-sensor, including an indication of where a capillary channel is placed over the respective micro-sensors.

FIG. 6 shows the position and area of two examples of dried reagent 303 for a blood coagulation test assay deposited on an unaltered surface material 301 adjacent to a micro cantilever based micro sensor 405, having a gap between the micro-sensor and regarding deposition site 304, including an indication 406 of where a capillary channel is placed over the respective micro-sensors to form the final test strip device. In both cases, the reagent has been deposited using the same liquid dispense method, and is the same reagent constitution and volume. Again, it can be seen that the reagent deposition is highly variable. This figure therefore clearly shows the position of the reagent deposition site, relative to the micro-cantilever sensor 405, i.e. adjacent the end of the micro-cantilever which is operable to sweep through a volume of fluid under test subsequently drawn up a capillary in the area denoted by lines 406. It can be seen that the fluid under test will mix with the reagents deposited on the deposition site, aided by the movements of the micro-cantilever sensor(s) 405. Whilst micro-cantilevers type sensors are shown, the invention is not so limited.

Control of the variation in surface area and location of deposition can, to a certain extent, be achieved by slowing down the manufacturing process and accepting a poorer yield of test strips. This is done by only depositing very small amounts of reagent per pass of the deposition equipment over each test strip, and building up the total amount of reagent required by multiple passes of a deposition head. However, the level of control is low, and increases production costs and time considerably.

If the location of the chemistry deposition is incorrect, the bulk of the deposited chemistry will be too far from where it actually needs to be to influence the test—i.e. near a fluidic channel operable to channel the fluid under test (in combination with the reagent) to the actual sensor, in the test chamber. By discounting areas of chemistry too far away from the fluidic channel, it can be seen that inaccurate location of the deposition will also lead to variability in both the volume and surface area of the chemistry.

Meanwhile, variations of surface area and volume of reagent are sources of variability in tests, because surface area influences the speed at which the chemistry can be absorbed into the fluid under test and the volume of the chemistry deposited in an area also influences the rate of uptake and final concentration of chemistry in the fluid under test.

Accuracy, uniformity and speed of reagent deposition may be improved by using suitably patterned deposition sites. Thus, example embodiments of the present invention provide a solution to the above described problems in the prior art by providing a deposition site comprising an island of material concentrically surrounded by at least one moat defining the shape of the island. Preferably, dependent on reagent chemistry, volume, surface material deposition area available, and the like, there is provided further moat and/or fences concentrically surrounding the first fence. The total number of moats and fences may be between 1 and 5, preferably between 1 and 3, and there may be more or less moats than fences, or vice versa. The number of moats and fences, and their shape and dimensions, have been varied on different designs, and their performance for specified reagent chemistry and surface material type/properties have been described in more detail below.

Figure 8:
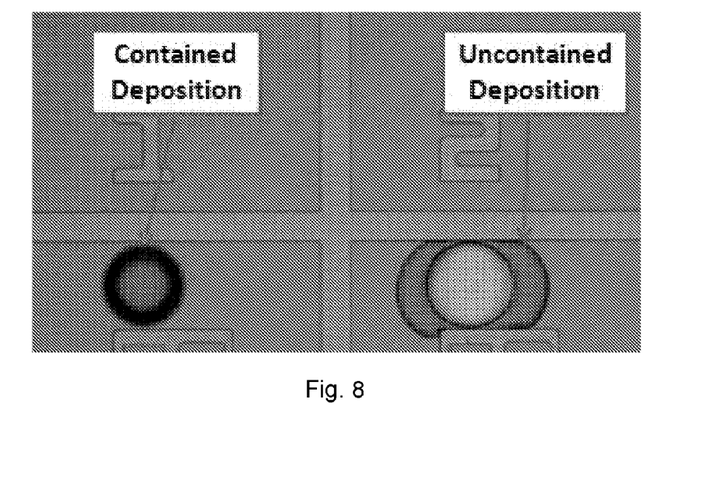
FIG. 8 shows the effectiveness of surface material patterning according to an example embodiment of the invention in which the left-hand figure is patterned according to at least one embodiment of the invention and the right-hand figure is a basic well structure.

An initial choice for holding chemistry deposition in a specific location is to put a well into the test strip surface material which is then used to contain the deposited chemistry. An example of such a formation is shown in FIG. 8 (on the right hand side). However, for hydrophilic surface materials, it was found that this did not work to contain the reagent chemistry, as shown. In the example of FIG. 8, the hydrophilic nature of the surface material means that when the chemistry reaches the edge of the well, it does not stop flowing as it continues to be energetically favourable to spread across the sensor surface material.

Figure 7:
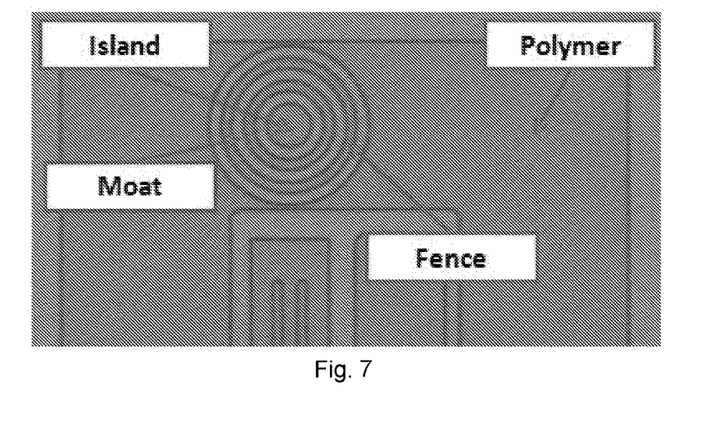
FIG. 7 shows a surface material formation (e.g. patterning) for improving the accuracy and consistency of a deposition of a reagent according to an example embodiment of the present invention.

FIG. 7 shows an altered surface material formation, i.e. a patterned deposition site, for improving the accuracy and consistency of a deposition of a reagent according to an example embodiment of the present invention. In this embodiment, the deposition site formation comprises a central circular 'island', surrounded by multiple 'fences' and 'moats', where an 'island' is an area of surface material left in place, a 'fence' is an annular ring of surface material left in place, and a 'moat' is an annular ring where the surface material is removed (such as by etching, stamping, or the like) where 'moats' are between an 'island' and 'fence', or between different 'fences'. Other scaling of the formation is also envisaged. In this example, the surface material is a polymer, but the invention is not limited to any specific surface material. Other deposition site formations are also envisaged, as will be described in more detail below, dependent on the particular use case. For example, a single island and moat with no fence structures can be used if the contact angle is above an intended range or the volume dispensed is lower than an intended range.

The fences may be at least partially etched to result in a lower height relative to the original substrate height. The pattern may also be created in photo-definable polymers or moulded or machined.

FIG. 8 shows the effectiveness of a surface material deposition site formation according to an example embodiment of the invention (comprising an island, with surrounding moats and fences, on the left of the figure), compared to a simple well deposition site formation (on the right). The surface material used was hydrophilic (by application of a suitable surface treatment), and the reagent fluid was water based. The same amount of fluid was used in both cases. It can be seen that the island and moat deposition site formation has contained the reagent, whereas the simple well formation has not.

Figure 9:
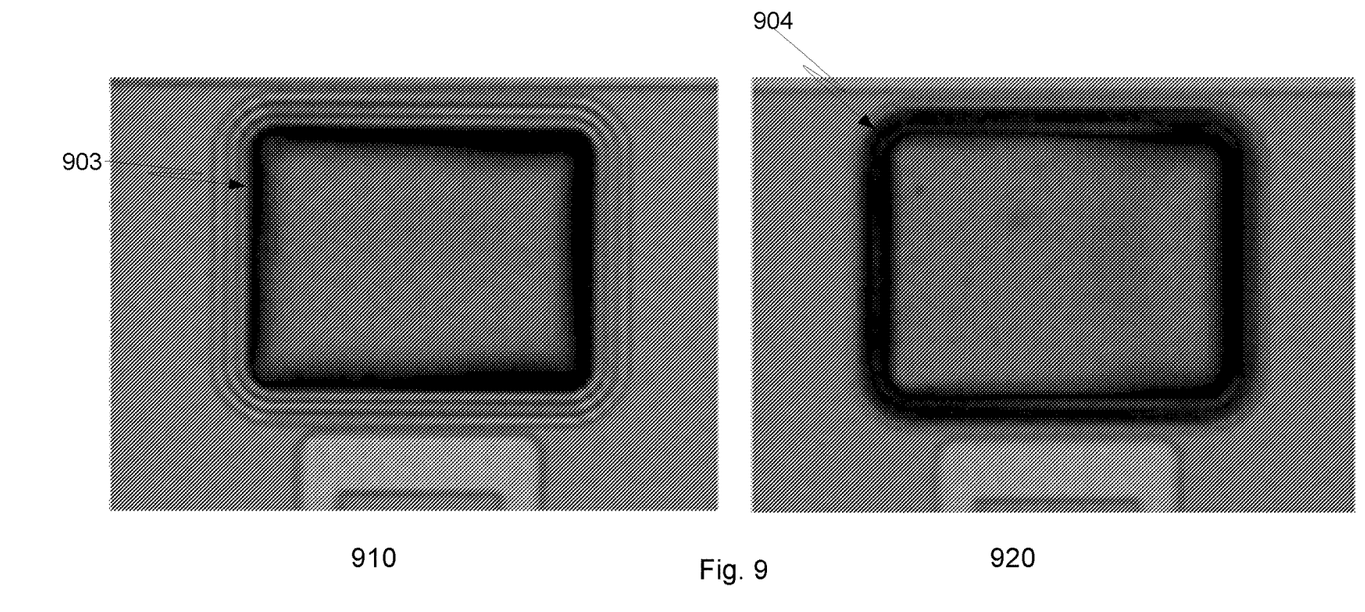
FIG. 9 shows alternative embodiments of surface material formations according the invention.

FIG. 9 shows the benefit of using multiple moat/fence structures to contain a reagent fluid deposition. In particular, the figure illustrates how a fluid deposition may be tightly contained, even if it breaches one or more of the moat/fence boundaries due to non-ideal conditions. For example, this may be useful if the contact angle of the surface material is slightly lower than the intended useful range, because the position of the reagent is still maintained while the variation in area is minimal. In the left-hand FIG. 910, a multi-moat/ fence patterned deposition site (having a central island, three moats and three fences all in a rectangular, but curved corner shape) contains a chemistry deposition at the edge of the island 903 and thus would have no need of the outer moats and fences per se.

However, in the right-hand figure 920, an image of the same design of deposition site is shown in which a similar chemistry deposition has overflowed the central island, but then been contained by one of the moat or fence 904 constructs of the multi-moat/fence structure. In this case, had an island and single moat been used, the deposition would most likely have failed to have been contained. Such a situation may occur due to the volume of reagent fluid being above a certain threshold, surface contamination bridging the island and first fence structure, or the like, imperfect fabrication or other non-ideal usage conditions. Therefore, the redundancy of multi-moat/fence patterned deposition sites is useful, especially since the method of forming the island, moats and fences is typically an etching or stamping process, so there would be no additional manufacturing cost for the redundancy beyond the additional footprint of the sensor chip. Accordingly, by using suitably patterned deposition sites comprising at least one island and a moat, the majority of test strips may be manufactured quickly, yet still with suitable accuracy of deposition. The number of moats and fences may be related to a WCA of the surface material (e.g. if the WCA is below a certain figure, then a single moat is sufficient, but if it is above another figure, then more moat/fences are advisable) and/or high(er) volumes of reagent being deposited (either absolute, or per deposition drop/deposition head pass). Put another way, if the WCA is below the range of useful containment for the volume intended, then multiple moat/fence structures have an advantage.

It is important to observe at this point that the success or failure described here of a particular design is not a binary issue. Many of the designs can contain a particular specified chemistry of deposition, but may fail to do so at sufficiently higher than intended volumes of chemistry deposition or with sufficient reliability for a process which may be used in the manufacture of millions of test strips containing the reagent deposition. Accordingly, the size of the deposition site and the number of surrounding fences and moats may be varied according to the particular use case (e.g. reagent type, reagent deposition volume, desired deposition surface area, and the like). Thus, when depositing smaller volumes on small areas, single islands can be sufficient to capture a full deposition. However, as more deposition volume is needed, moats and fences may be added, as required. A safety margin may be provided by providing more moats/fences that might strictly be required. Moreover, in many use cases, the area provided near/adjacent the micro-sensor for depositing reagent may be limited and/or fixed in order to limit the total area of the, for example, monolithically integrated micro-sensor test strip system overall. In these cases, the addition of further moats and or fences has to reduce the area available for the central "island", i.e. adding moats and or fences "eats into" the deposition site island central area. In these situations, it has been found that as the % area of the moat/fences compared to the area of the deposition site as a whole increases, the efficiency of the moat/fences can reduce. Thus, it has been found that keeping the moat/fences between 10% and 40% by total area of the deposition site is advantageous.

As an example, where the total deposition site formation is to be between 300 and 600 microns wide, and the particular manufacturing process used allows formations to have a minimum defined size of 10 microns, a single moat and fence may use 10 to 20% of the total deposition site area, two moat/fences may use 20 to 35% and three moat/fences may use 30 to 45% of the total deposition site area. Changing the manufacturing process used, so that smaller (or indeed larger) minimum defined geometry sizes apply may alter the % of the total deposition site area taken up by the respective fences and moats. Smaller process geometries generally increases manufacturing costs, whilst using larger process geometries can reduce costs. When producing millions of test strips according to embodiments of the invention, the manufacturing costs can be an important factor, and the number of fences/moats may be altered to account for, for example, using a lower cost process geometry.

Figure 10:
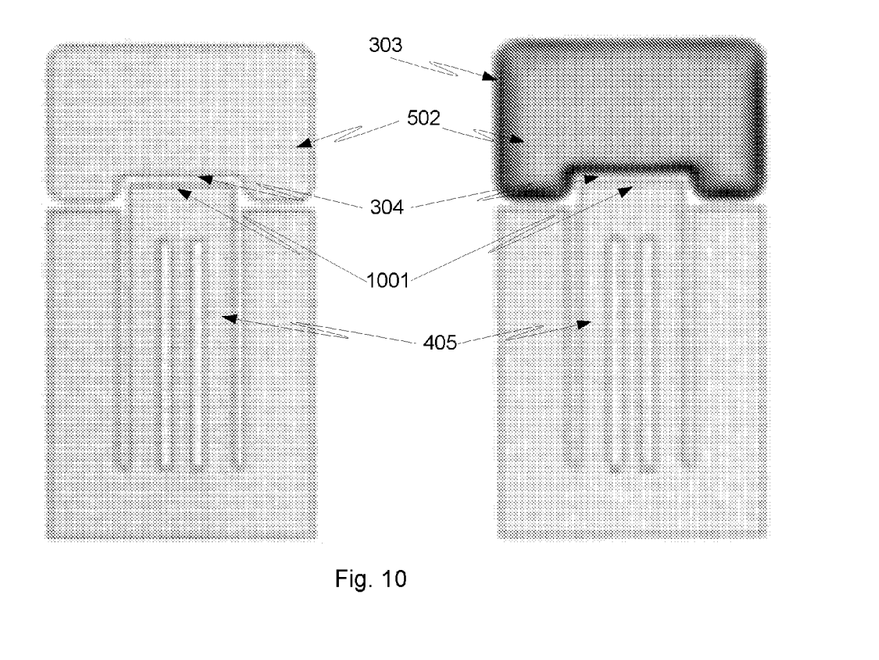
FIG. 10 shows another example embodiment of a surface material formation according the invention, pre and post deposition.

FIG. 10 shows another advantage of the present invention, namely the ability to form the deposition site in any arbitrary shape and at any arbitrary position, to thereby improve the performance of the overall micro-sensor based test strip. This is because it is now possible to optimise the reagent placement position and formation, to, for example, increase the rate of interaction between the reagent and fluid under test near the micro-sensor. In the example shown in FIG. 10, a single island is used, as it is sufficient to retain the reagent deposit at the deposition volumes used, however moats/fences may have been used in different circumstances, such as higher deposition volumes, lower WCA, etc. The left hand figure shows the deposition site 502 prior to deposition occurring, whilst the right hand figure is post deposition, showing the deposited reagent 303 is uniformly deposited on the irregularly shaped deposition site formation of the present invention.

In the example shown in FIG. 10, which uses a micro-cantilever 405 based sensor having a "most sensitive" portion at its tip 1001, the deposition site 502 (comprising a single island and moat defining the island) is shaped so that the deposition site encompasses the tip end of the micro-cantilever. Thus reagent is surrounding the tip, therefore when the fluid under test enters the capillary above the sensor, it makes contact with the reagent on all sides around the most sensitive part of the cantilever, the tip 1001, and strengthens the reaction around this most sensitive region and improves the reaction time, and the like.

Figure 11:
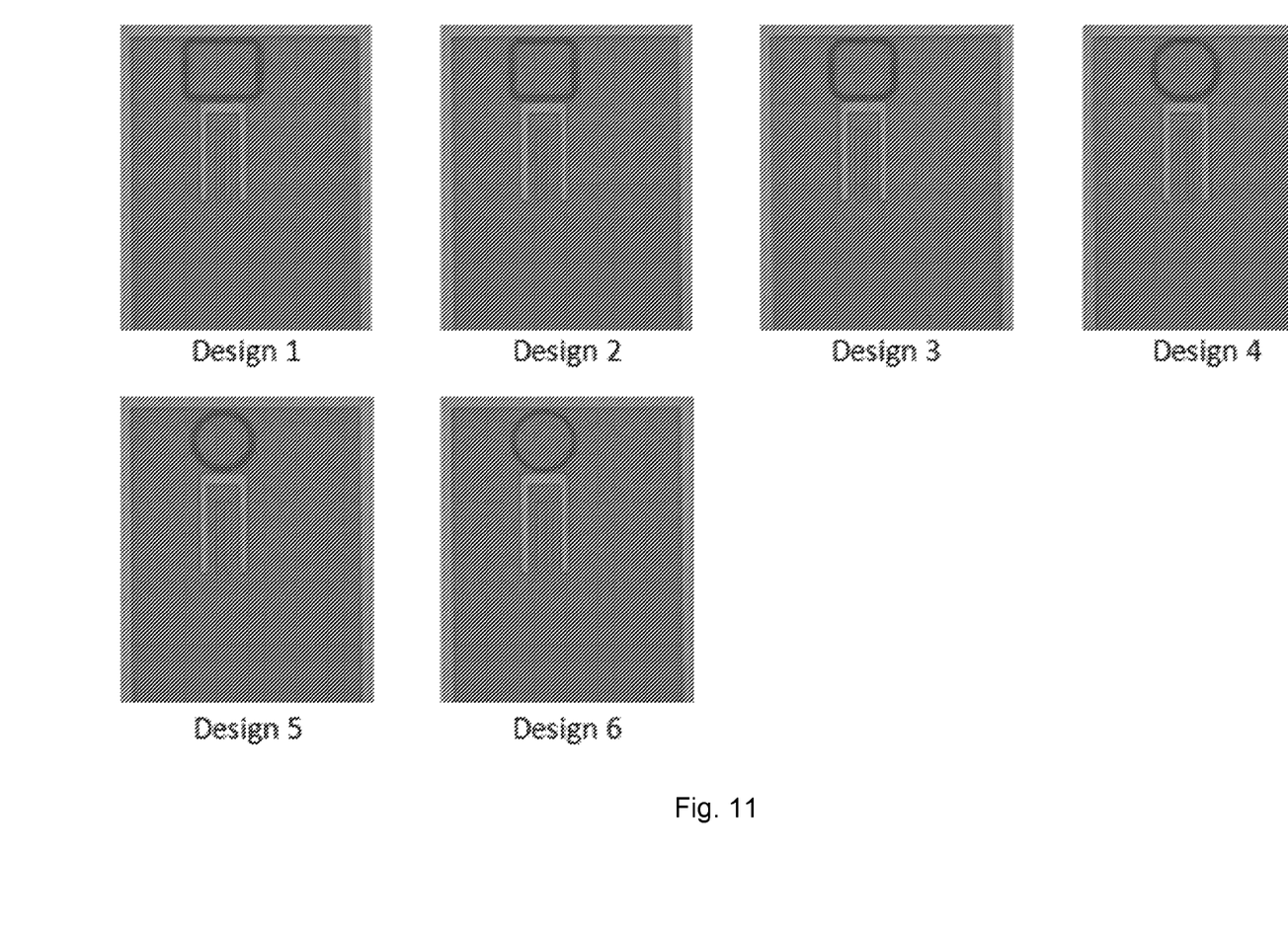
FIG. 11 shows still further example embodiments of surface material formations according the invention.

FIG. 11 shows a further selection of deposition site designs, for use in a single micro-cantilever test strip design. They may equally be used for other micro-sensor types/formations. Designs 1 to 5 are multi-moat/fence designs with three moats and two fences each. Again, it can be seen from this figure that different shapes of overall deposition site (i.e. the island and respective moats/fences) may be used. For example, design 1 is a rounded off rectangular shape, design 2 is a rounded off square shape, design 3 is an even more rounded off square shape, design 4 is an elongated circular shape, and design 5 is a circular shape. Design 6 contains only two moats and one fence.

Many methods exist to create patterns on substrates, but micro-fabrication using photolithographic printing, stamping and plasma etching are all particularly reproducible methods to form the island and one or more moat (and fence(s)). They are also particularly suitable for mass manufacture of test sensor strips that are formed from a monolithically integrated sensor and deposition site. Alternative methods of manufacturing the designs may include, but are not limited to: photodefinable polymers, laser etching of polymer, polymer imprint/stamping, micro-machining, and the equivalents.

Example embodiments of the present invention include methods of forming a test strip, and the resultant test strips themselves, which may provide the following benefits:

Uniformity—the patterned deposition site forces the deposited volume (of reagent, or other fluid) into a defined area. The area uniformity of the deposition is therefore controlled regardless of the variation in surface hydrophobicity or hydrophilicity from test strip to test strip, and/or the relative humidity of the ambient environment during use or manufacture. This means that from test strip to test strip, the deposition chemistry is correctly and accurately placed and near identical in area, so that it can be absorbed into the fluid under test more reproducibly, under similar timescales and to the same concentration.

Location—the patterning locks the location of the deposited chemistry into a well-defined location, which is particularly advantageous in a microfluidic system using the deposition site for containing, for example, reagents to be introduced to the fluid under test, so that the test strip can detect different parameters of the fluid under test-reagent reaction, which may be at least partially limited by the rate of diffusion of the reagent into the fluid under test. Reduction in the variation in location of the reagent chemistry deposition may reduce the variation in time of the responses of the sensors formed on the respective test trips to physical changes in the immediate vicinity. The reduced variation in deposited chemistry location ensures lower variation in the effective amount of chemistry in contact with the fluid under test, where the fluid under test is channelled by a $2^{nd}$ component aligned to the micro-sensor substrate.

Shape—surface patterning can be created to deliberately guide the deposited chemistry into predetermined shapes (that are advantageous to the test used) and/or into confined areas that are unachievable by deposition alone, for example, an encompassing shape as seen in FIG. 10, which can enhance reaction strength around the region of sensitivity of the micro-cantilever based micro-sensor.

Monolithic architecture—where the particular sensors being used on the test strip may be at least partially formed from the same substrate material as the test strip (for example, when using one or more micro-cantilever sensors formed from polymers having different coefficients of expansion, that are activated through a heat based actuator and the resultant movement detected using a movement sensor, such as piezoresistive or piezoelectric material), the patterning may be performed in/on the same material and as part of the same process as used to form the sensor, thereby significantly reducing complexity and eliminating additional production issues and costs. The same effects may also be achieved in material layers added specifically for the purpose of creating patterned deposition sites, but the simplicity of the monolithic solution makes it more favourable to produce both the test sensors and deposition sites in the same process.

Surface treatment—the above-described deposition site patterning may be performed on the test strip substrate material, such as polymer, which is suitable for surface treatments to it give a variety of hydrophilic or hydrophobic surface properties. The patterned deposition sites may prevent the surface treatment dependent variation in size and uniformity of the deposition that would normally be seen on un-patterned surfaces from determining the final surface area of the (reagent) deposition. This is the say, example embodiments of the invention allow any type of surface treatment (or variability in surface treatment) of the test strip substrate material to be used, whilst still providing a uniform deposition area. The area of the patterned deposition site(s) may be chosen to best suit the relevant range of contact angles of the surface material expected to be seen, the volumes of deposited reagent/fluid to be used, or as a result of the particular surface treatment being used.

Production Efficiency—the patterned deposition sites may ensure that the (reagent) chemistry deposition on the sensor test strip can be performed rapidly, and even with reagent chemistry fluid deposition equipment having a lower accuracy of deposition (i.e. the fluid deposition equipment used to create the test strips does not need to be so accurate, as the deposition site controls the shape of the end result). Deviations of the deposited chemistry from the centre of the desired location can be better tolerated with the deposition site formations according to example embodiments of the invention, than without.

By providing controlled deposition of wet chemistry onto planar surfaces, it is possible to create, for example, an improved sensor test chip having a functional fluidic sensor (e.g. of a MEMS type cantilever fluidic probe) formed thereon, with suitable accurately deposited chemistry in a microfluidic environment. This is because the performance of the complete functional system of such microfluidic sensor test chips may be highly dependent on the (reagent) chemistry deposition and, in addition to its chemical composition, the control of physical aspects (size, location, area) may be critical in obtaining repeatable results.

Multiple deposition sites could be used to allow, for example multiple fluids to be deposited in close proximity to the (one or more) sensors on separate, but tightly spaced deposition sites thereby allowing mixing of the chemistries to occur after the fluid under test has filled the micro-sensor test strip. This may be particularly beneficial for chemistries where it is beneficial to prevent components from mixing until the test starts.

Additionally, there could be multiple sensors with multiple deposition sites which are later separated into individual chambers with the addition of another strip component.

Whilst the foregoing has been described in terms of reagent deposition for a microfluidic test sensor, it may also be used in any other situation requiring accurate deposition of fluids onto a substrate.

The described method of forming deposition sites on a test strip may also be implemented as a computer program for running on a computer system controlling a test strip manufacturing process, at least including executable code portions for performing steps of any method according to embodiments the invention when run on a programmable manufacturing control apparatus, such as test sensor manufacturing equipment.

A computer program may be formed of a list of executable instructions such as a particular application program and/or an operating system. The computer program may for example include one or more of: a subroutine, a function, a procedure, an object method, an object implementation, an executable application, an applet, a servlet, a source code, an object code, a shared library/dynamic load library and/or other sequence of instructions designed for execution on a suitable computer system.

The computer program may be stored internally on a computer readable storage medium or transmitted to the computer system via a computer readable transmission medium. All or some of the computer program may be provided on computer readable media permanently, removably or remotely coupled to the programmable apparatus, such as an information processing system. The computer readable media may include, for example and without limitation, any one or more of the following: magnetic storage media including disk and tape storage media; optical storage media such as compact disk media (e.g., CD-ROM, CD-R, Blueray, etc.) digital video disk storage media (DVD, DVD-R, DVD-RW, etc) or high density optical media (e.g. Blu-eray, etc); non-volatile memory storage media including semiconductor-based memory units such as FLASH memory, EEPROM, EPROM, ROM; ferromagnetic digital memories; MRAM; volatile storage media including registers, buffers or caches, main memory, RAM, DRAM, DDR RAM etc.; and data transmission media including computer networks, point-to-point telecommunication equipment, and carrier wave transmission media, and the like. Embodiments of the invention are not limited to the form of computer readable media used.

In the foregoing specification, the invention has been described with reference to specific examples of embodiments of the invention. It will, however, be evident that various modifications and changes may be made therein without departing from the broader scope of the invention as set forth in the appended claims.

Also for example, the examples, or portions thereof, may implemented as soft or code representations of physical circuitry or of logical representations convertible into physical circuitry, such as in a hardware description language of any appropriate type, for use in controlling the manufacture of test strips, or similar, having controlled deposition sites.

However, other modifications, variations and alternatives are also possible. The specifications and drawings are, accordingly, to be regarded in an illustrative rather than in a restrictive sense.

Unless otherwise stated as incompatible or the physics or otherwise of the embodiments prevent such a combination, the features of the following claims may be integrated together in any suitable and beneficial arrangement. This is to say that the combination of features is not limited by the specific claim form listed, particularly the form of the dependent claims.

The invention claimed is:

1. A fluid test strip, comprising:
   a micro-sensor formed on a substrate surface, wherein the micro-sensor comprises a micro-cantilever; and
   a reagent deposition site formed on the substrate surface, operable to control the size and location of a reagent deposition;
   wherein the deposition site comprises a central island portion, annularly surrounded by a portion of non-existent surface material; and
   wherein the reagent deposition site is formed adjacent the micro-sensor.

2. The fluid test strip of claim 1, wherein the reagent deposition site is formed in a predetermined shape beneficial to the operation of the micro-sensor.

3. The fluid test strip of claim 2, wherein the predetermined shape comprises a shape operable to encompass at least a portion of the micro sensor.

4. The fluid test strip of claim 2, wherein the predetermined shape comprises a portion encompassing a sensitive end of the micro-cantilever.

5. The fluid test strip of claim 1, wherein a portion of non-existent surface material comprises a moat.

6. The fluid test strip of claim 1, further comprising at least one fence, wherein a fence comprises a portion of the surface material annular surrounding a portion of non-existent surface material.

7. The fluid test strip of claim 6, wherein the at least one fence comprises multiple moats and fences, each numbered in the range of 1 to 3.

8. The fluid test strip of claim 1, wherein the at last one moat comprises between one and three moats and the at least one fence comprises between one and three fences.

9. The fluid test strip of claim 1, wherein the micro-sensor is operable to detect changes in a fluid under test as a result of a reaction between the fluid under test and one or more reagents deposited in the deposition site.

10. The fluid test strip of claim 1, wherein the reagent deposition site comprises a fixed area.

11. The fluid test strip of claim 10, wherein any moats and/or fences comprises up to 40% of the total deposition area.

12. The fluid test strip of claim 1, wherein the deposition site is formed dependent upon one or more of:
    a contact angle of the surface material;
    a volume of deposited reagent fluid;
    a hydrophilicity of the surface material;
    a hydrophobicity of the surface material;
    a surface energy of the surface material;
    a surface treatment of the surface material.

13. The fluid test strip of claim 1, further comprising multiple deposition sites within the vicinity of one or more micro-sensors.

14. A method of forming fluid test strip, comprising:
    forming a micro-sensor on a substrate surface, wherein the micro-sensor comprises a micro-cantilever; and
    forming a reagent deposition site on the substrate surface, operable to control the size and location of a reagent deposition;
    wherein forming the reagent deposition site further comprises forming the deposition site to have a central island portion, annularly surrounded by a portion of non-existent surface material; and
    the method further comprising forming the reagent deposition site adjacent the micro-sensor.

15. The method of claim 14, further comprising forming the reagent deposition site in a predetermined shape beneficial to the response of the micro-sensor to the specific test.

16. The method of claim 14, wherein the predetermined shape comprises a shape operable to encompass at least a portion of the micro-sensor.

17. The method of claim 14, wherein the predetermined shape comprises a portion encompassing a sensitive end of the micro-cantilever.

18. The method of claim 14, wherein a portion of non-existent surface material comprises a moat.

19. A computer-readable medium comprising instructions, which, when executed by a processor connected to a test strip manufacturing apparatus, cause the apparatus to carry out the method of claim 14.

* * * * *